United States Patent [19]

Bergkuist et al.

[11] Patent Number: 4,997,627

[45] Date of Patent: Mar. 5, 1991

[54] SAMPLE ANALYSIS

[75] Inventors: Carolyn Bergkuist, Hampstead, N.H.; Yvonne Fraticelli, Newton; Theodore S. Geiselman, Groveland, both of Mass.

[73] Assignee: Fisher Scientific Company, Pittsburgh, Pa.

[21] Appl. No.: 74,882

[22] Filed: Jul. 17, 1987

[51] Int. Cl.[5] .......................................... G01N 35/00
[52] U.S. Cl. ...................................... 422/81; 422/67; 436/52; 435/288; 435/289
[58] Field of Search ...................... 422/67, 81; 436/52; 435/12, 14, 288, 289, 290; 204/1.11, 1.14, 1.17, 1.12, 400, 403, 415, 416, 418, 419

[56] References Cited

U.S. PATENT DOCUMENTS

| | | | |
|---|---|---|---|
| 3,915,804 | 10/1975 | Messing . | |
| 3,926,734 | 12/1975 | Gray . | |
| 3,950,226 | 4/1976 | Chang . | |
| 4,153,513 | 5/1979 | Edelmann et al. | 435/288 |
| 4,197,369 | 4/1980 | Weaver . | |
| 4,263,406 | 4/1981 | Bostick . | |
| 4,277,560 | 7/1981 | Gray et al. | 422/81 |
| 4,420,564 | 12/1983 | Tsuji et al. | 204/403 |
| 4,443,407 | 4/1984 | Weinberg et al. | 436/52 |
| 4,476,005 | 10/1984 | Tokinaga . | |
| 4,490,235 | 12/1984 | Calzi | 204/411 |
| 4,507,338 | 3/1985 | Tabacco . | |
| 4,525,265 | 6/1985 | Abe et al. | 204/403 |
| 4,640,821 | 2/1987 | Mody et al. | 436/52 |
| 4,759,828 | 7/1988 | Young et al. | 204/403 |

FOREIGN PATENT DOCUMENTS 0101236 8/1983 European Pat. Off. .
9109198 12/1982 Japan .
58-209996 12/1983 Japan .

OTHER PUBLICATIONS

Schindler, "A NH4-Selective-Enzymatic Flow-Through System", J. Clin. Chem. Clin. Biochem., vol. 16, 1987, pp. 447–450.
Leon, Lois P. "Continuous-Flow Analysis for Glucose in Serum, with Use of Hexokinase and Glucose-6-Phosphate Dehydrogenase Co-immobilized in Tubular Form", Clin. Chem., 26/1, 123–129 (1980).
Mascini, Marco, "A Flow Through Detector for Simultaneous Determination of Glucose and Urea in Serum Samples", Analytica Chimica Acta, 159 (1984), 71–72.
Pacakova, Vera "Use of the Clark Oxygen Sensor with Immobilized Enzymes for Determinations in Flow Systems", Analytica Chimica Acta, 159 (1984), 71–79.
*Analytical Chemistry*, vol. 55, No. 11, Sep. 1983, Columbus US, pp. 1040–1053; J. Ruzicka: "*Flow Injection Analysis, from Test Tube to Integrated Microconduits*".

Primary Examiner—Robert J. Warden
Assistant Examiner—D. John Griffith, Jr.
Attorney, Agent, or Firm—Fish & Richardson

[57] ABSTRACT

A system for analyzing a biological fluid or the like for a constituent of interest comprises structure defining a sample inlet port, structure defining an analysis region, a measuring system connected in sensing relation to the analysis region, and structure defining a reaction chamber that has an immobilized enzyme capable of modifying the constituent of interest. Control means operates liquid flow means in a unidirectional sample flow mode to initially flow a sample of material to be analyzed from the sample inlet port to the reaction chamber and to the analysis region for a measurement of unmodified sample material, and then operates the liquid flow means in a bidirectional sample flow mode to oscillate the sample material in the reaction chamber and facilitate modification by the immobilized enzyme of the constituent of material in the sample. Modified sample material is then introduced into the analysis region and the measuring system is operated to obtain a measurement of modified sample material, the measurements of modified and unmodified sample material then being used to provide an indication of the amount of the constituent of interest in the sample material.

23 Claims, 1 Drawing Sheet

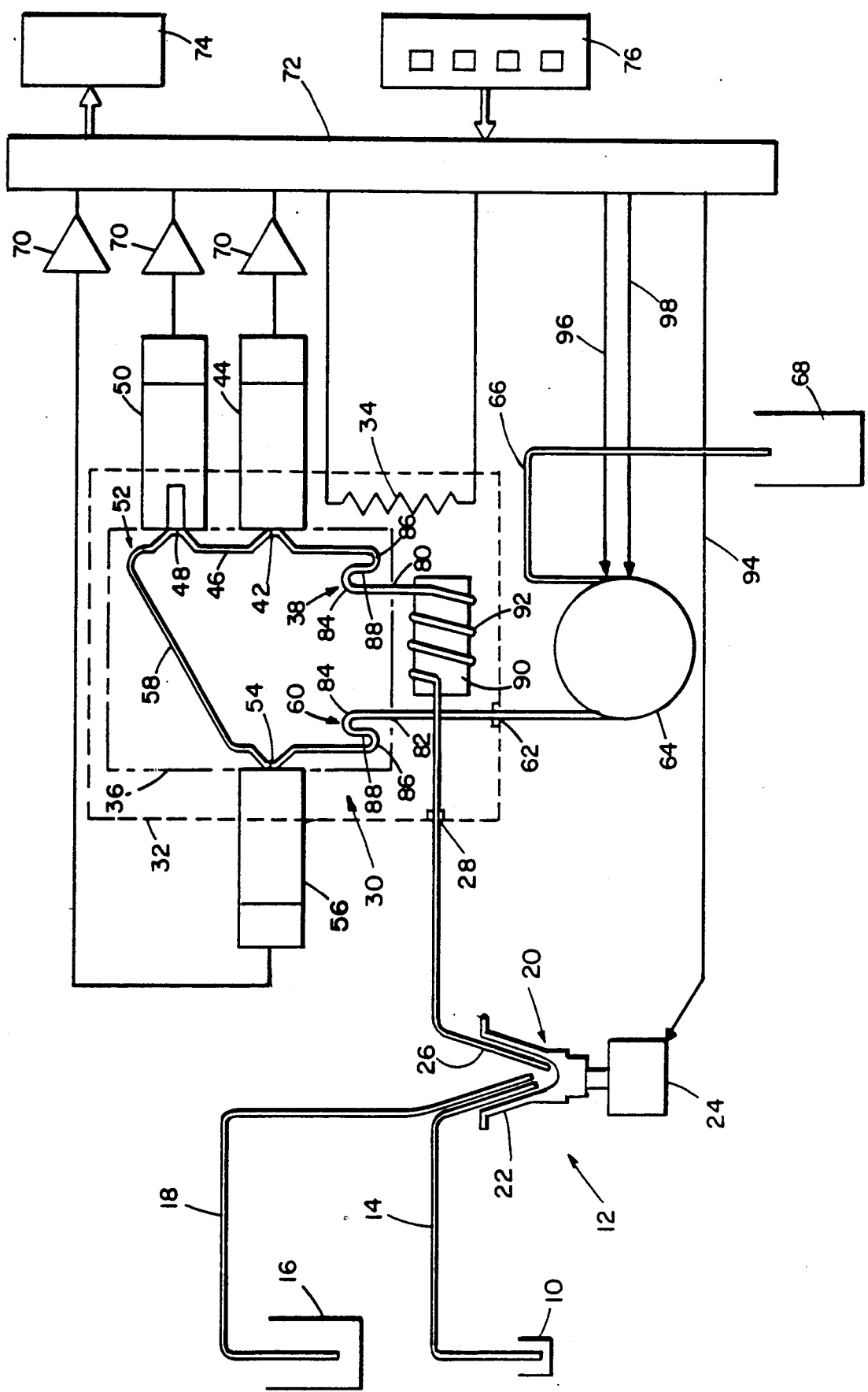

SAMPLE ANALYSIS

This invention relates to methods and apparatus for the analysis of fluid samples and has particular application to methods and apparatus for analysis of parameters of biological fluids such as blood.

Accurate measurement of one or more constituents of a sample of biological fluid (whole blood, plasma, serum, urine, etc.) provides useful information for diagnosis, assistance in the control of life support devices, evaluation of the effectiveness of therapeutic measures, and the like. Various electrodes including polarographic electrodes and ion selective electrodes have been used in such constituent measurements. An immobilized enzyme has also been used to convert a constituent of interest in the sample to an ion detectable by the electrode, for example, urea may be enzymatically converted to ammonium ions which are detectable by an ammonium electrode. One problem with such measurements, however, is that another constituent, such as an interfering ion, present in the sample may contribute to the total output from the electrode, resulting in an erroneous indication of the amount of the constituent of interest present in the sample.

In accordance with one aspect of the invention, there is provided a system for analyzing a biological fluid or the like for a constituent of interest that comprises structure defining a sample inlet port, structure defining an analysis region, a measuring system connected in sensing relation to the analysis region, and structure defining a reaction chamber with immobilized enzyme in the reaction chamber that is capable of converting the constituent of interest to a constituent detectable by the measuring system. Control means operates liquid flow means in a unidirectional sample flow mode to initially flow a sample of material to be analyzed from the sample inlet port to the reaction chamber and to the analysis region for a measurement of unmodified sample material, then operates the liquid flow means in a bidirectional sample flow mode to oscillate the sample material in the reaction chamber and facilitate modification by the immobilized enzyme of the constituent of material in the sample constituent. Modified sample material is then introduced into the analysis region and the measuring system is operated to obtain a measurement of modified sample material, the measurements of modified and unmodified sample material being used to provide an indication of the amount of the constituent of interest in the sample material, the first measurement preferably being effectively subtracted from the second measurement.

In a preferred embodiment, the liquid flow means is a positive displacement pump that is connected to a series flow path, the sample inlet port structure is connected to the inlet of the reaction chamber, the outlet of the reaction chamber is connected to the inlet of the analysis region, and the analysis region has a polarographic electrode, an ion selective electrode, and a reference electrode, and the measuring and reference electrodes are spaced from one another by a flow path portion located so that the reference electrode is downstream and spaced from the measuring electrode by a flow path volume greater than the displacement volume that sample material is moved by the pump during the bidirectional mode sample flow interval. The control means operates the pump first in the unidirectional sample flow mode to rapidly flow (at a rate of at least about one hundred microliters per second) a sample of material to be analyzed from the sample inlet port through the reaction chamber to the analysis region for a measurement of unmodified sample material, then in the bidirectional sample flow mode to oscillate the sample material in the reaction chamber and analysis region, and then again operates the pump in the unidirectional sample flow mode to flow the sample from the reaction chamber to the analysis region for a measurement of modified sample material.

In a particular embodiment, the reaction chamber has a volume of about two hundred microliters and is in the form of an elongated tube (about twenty five centimeters long) that is disposed in coil or serpentine form on a temperature stabilizing member; glucose oxidase and urease enzymes are coimmobilized on the inner surface of the tube; the polarographic electrode senses oxygen and the ion selective electrode includes nonactin ionophore for sensing ammonium ions. Flow path sections that are about three centimeters long connect the reaction chamber tube to the oxygen sensing electrode and similarly connect the ammonium sensing and reference electrodes. The analysis portions of the oxygen sensing, ammonium sensing and reference electrodes and the reaction chamber tube are housed in a temperature controlled environment that is maintained at an elevated temperature such as about 33° C.

In accordance with another aspect of the invention, there is provided a method of measuring a substance capable of being enzymatically modified that includes the steps of providing a reaction chamber that contains an immobilized enzyme capable of modifying a substance of interest, providing an analysis region spaced from the reaction chamber that includes detecting means, exposing sample material to the detecting means before the enzyme has modified the substance and providing a first output as a function of the sensed unmodified sample material, exposing the sample material to the enzyme to modify the substance of interest, then exposing the modified sample material to the detecting means and producing a second output as a function of the quantity of a constituent in the modified sample material, and processing the first and second outputs to provide an indication of the amount of the substance of interest in the sample.

In a particular embodiment, there is provided a method of measuring urea that is capable of being enzymatically converted to ammonium ions with compensation for potassium ion interference that includes the steps of contacting the sample with an ammonium ion detecting electrode before the enzyme has converted the urea to ammonium ions and measuring the output of the ion detecting electrode to provide an indication of the potassium ion interference of the sample; contacting the sample with the ion detecting electrode after the enzyme has converted urea to ammonium ions and measuring the output of the ion detecting electrode to determine the apparent amount of urea in the sample; and effectively subtracting the potassium ion interference output from the apparent urea output to determine the amount of the urea in the sample. The method preferably further comprises the step of calibrating the detecting means using first and second calibrators having known concentrations of potassium ions and urea by contacting the first and second calibrators individually with the detecting means and measuring the output of the detecting means before and after the enzyme has converted the urea in the calibrators to ammonium ions.

In accordance with another aspect of the invention, there is provided an analysis system for measuring the plurality of parameters of a fluid sample that includes housing structure, and a flow-through cell in the housing in which an inlet port, an outlet port, and at least two sensor accepting ports are defined. Structure in the cell defines a sample flow path through the flow-through cell that is disposed in a generally vertical plane and that serially connects the inlet port, the sensor ports and the outlet port, and that includes a first serpentine flow path portion between the inlet port and a first sensor port and a second serpentine portion between the last sensor port and the outlet port. The serpentine portions provide isolation for the sensor ports. Preferably, the flow-through cell is of transparent material such that fluid sample in said flow path may be visually observed.

In preferred embodiments, each serpentine flow path portion includes a downwardly curved portion and an upwardly curved portion, with an intervening vertical transition section. In a particular embodiment, each downwardly curved and upwardly curved portion is of about 180° extent and extends along an arc of less than one centimeter diameter and the vertical transition section is less than one centimeter long. Further, the sample flow path includes a first section that extends generally upwardly from the first serpentine flow path portion to a first sensing cavity, a second section that extends generally downwardly from the last sensing cavity to the second serpentine flow path portion, and an isolation portion that extends from the first section to the second section and is inclined generally downwardly to provide an isolation section between the first and second portions.

Other features and advantages of the invention will be seen as the following description of a particular embodiment progresses, in conjunction with the drawing, which is a diagram of an analysis system in accordance with the invention.

DESCRIPTION OF PARTICULAR EMBODIMENT

The biological fluid analysis system shown in the drawing includes sample station 10 that is connected to mixing station 12 by conduit 14, and diluent reservoir 16 that is connected to mixing station 12 by conduit 18. In a particular embodiment, mixing station 12 employs a fluidic module of the type shown in Webster U.S. Pat. Nos. 4,304,257 and 4,601,881, the disclosures of which are specifically incorporated herein by reference. That module employs an array of valves and one or more metering chambers and is incorporated in a clinical analyzer embodiment of the type shown in copending application Ser. No. 074,942 entitled LIQUID HANDLING filed concurrently herewith, the disclosure of which is specifically incorporated by reference. Such a fluidic module can be used in place of the spin cup assembly employed in the embodiment described below.

Spin cup assembly 20 at station 12 includes funnel shaped spin cup 22 that is driven by reversible DC motor 24 located beneath the assembly. Diluent is flowed from reservoir 16 through tube 18 into spin cup 22 and sample is flowed from sample cup 10 through tube 14 into spin cup 22. Aspirator tube 26 is connected to inlet 28 of analysis unit 30.

Analysis unit 30 has a housing 32 in which heater structure (diagrammatically indicated at 34) is disposed, the heater being controlled to maintain a temperature of about 33° C. in housing 32. Also disposed within housing 32 is sensor module 36 that is fabricated from a clear, colorless (acrylic) material in which is formed a series flow path that extends from inlet port 80 through serpentine isolation loop 38 along a generally vertical path to analysis electrode port 42 to which oxygen sensing electrode 44 is coupled; then via flow path section 46 to analysis port 48 to which nonactin ionophore ammonium sensing electrode 50 is coupled; then via coupling flow path section 52 that extends from analysis port 48 to reference port 54 to which reference electrode 56 is coupled, flow path section 52 including downwardly inclined (at an angle of about 30°) isolation portion 58 that is about three centimeters long, and has a volume of about twenty microliters; and from port 54 through serpentine isolation loop section 60 to module outlet port 82. Each serpentine isolation loop section includes a downwardly curved portion 84 and an upwardly curved portion 86, each of about 180° extent along an arc of about 0.4 centimeter diameter and connected by a vertical transition section of about 0.5 centimeter length.

Sensor module 36 is fabricated from a clear colorless (acrylic) polymeric material and has a width of about seven centimeters, a height of about ten centimeters, and a thickness of about one centimeter. The flow passages are of about 0.8 millimeter in diameter and are formed within module 36 at a distance of about 0.3 centimeter from its front face. Module 36 is mounted in a generally vertical plane so that the flow path sections from the serpentine isolation portion 38 past the sensor ports 42 and 48 extend generally vertically upward, and the flow path section from sensor port 54 extends generally vertically downward.

Also disposed within housing 32 is aluminum temperature stabilizing cylinder 90 on which is disposed in coil form reaction chamber tube 92 that is about 25 centimeters long and has a capacity of about 150 microliters. Urease and glucose oxidase enzymes are coimmobilized on its inner surface. One end of tube 92 is connected to housing inlet 28 and its other end is connected to module inlet 80. The flow path extends from port 82 to housing outlet 62 and continues to peristaltic (or piston) pump 64. The outlet of pump 64 is connected by line 66 to waste container 68. The outputs of oxygen electrode assembly 44, ammonium electrode assembly 50 and reference electrode assembly 56 are applied via high impedance operational amplifiers 70 to control unit 72 for analogical interpretation and calculation of the activity and concentrations of ammonium ion and oxygen in the sample and transfer of resulting data to output device 74. An operator control (in the form of keyboard 76) is also coupled to controller 72.

In system operation, specified volumes of sample to be analyzed and diluent are transferred into mixing chamber spin cup 22. Controller 72 generates signals over line 94 to operate motor 24 to drive spin cup 22 in slow speed agitation to mix sample and diluent. After mixing, peristaltic pump 64 is operated in a fast flow mode (in response to controller signals on line 96) to pull diluted sample from cup 22 through aspirator tube 26 and reaction chamber coil 92 into the analysis and reference regions of electrodes 44, 50 and 56 at a flow rate of about 200 microliters per second. In this condition, a first portion of the diluted sample is in contact with the ammonium, oxygen and reference electrodes 44, 50, 56 while the reaction chamber coil 92 is filled with a second portion of the diluted sample, and that portion is in contact with the coimmobilized urease and glucose oxidase enzymes. Because of the rapid flow-through the reaction cell 92, the first portion contacting the electrodes 44, 50, 56 contains unconverted sample that has not been acted upon by the enzymes to convert urea to ammonium ions and to convert glucose to hydrogen peroxide.

Pump 64 is then operated in bidirectional mode (in response to controller signals on line 98) (alternate clockwise and counterclockwise directions of rotation) to oscillate the diluted sample portions in the analysis regions and the reaction chamber 92 back and forth over a distance of about one centimeter. This bidirectional flow mode promotes enzyme-sample contact within reaction chamber 92 and equilibration at electrodes 44, 50, 56. The bidirectional mode operation of pump is then terminated and the output from the electrodes 44, 50, 56 (in millivolts for ammonium electrode 44 and in picoamperes for oxygen electrode 50) is recorded by controller 72 to provide first data values (unconverted or pre-enzymatic reaction sample data—that is, data before urea in the sample has been converted to ammonium ions and glucose has been converted to hydrogen peroxide).

Following acquisition of these first data values, and after glucose and oxygen in the second diluted sample portion has reacted with the immobilized glucose oxidase enzyme to form gluconic acid and hydrogen peroxide and urea in the second diluted sample portion has reacted with the immobilized urease enzyme to form ammonium ions and carbon dioxide, pump 64 is operated in unidirectional flow mode (line 96) to pull the second diluted sample portion from reaction chamber 92 into the analysis regions of electrodes 44, 50 and 56. Pump 64 is again operated in bidirectional flow mode (line 98) to oscillate the sample portion in alternate directions to promote electrode equilibration. After that equilibration interval, a second set of data readings are taken, that data representing the apparent ammonium concentration in the converted sample mixture.

After the second set of data is collected, pump 64 is operated in unidirectional flow mode to discard the sample to waste 68 and the flow path is washed with buffer solution. The two sets of data provide (1) pre-enzymatic reaction (background) measurements representing interfering (primarily potassium ion in the case of electrode 50) contribution to the electrode response; and (2) post-enzymatic reaction measurements (representing apparent ammonium concentration—response to both ammonium and interfering ion contributions—in the case of electrode 50).

The actual concentration of glucose in the sample is determined by effectively subtracting pre-enzymatic reaction data from post-enzymatic reaction data. Similarly, the actual concentration of urea in the sample is determined by effectively subtracting pre-enzymatic reaction data from post-enzymatic reaction data using the following form of the Nicolsky equation:

$$\text{conc.}_{UN} = \text{antilog } [(E_S - E_{cal\,1})(1/S)] * \quad (1)$$

$$(Cal\,1_{UN} + kCal_{1k}) - (k\,\text{conc. } K)$$

where
 conc.$_{UN}$ = actual concentration of urea in the sample;
 $E_s$ = post-enzymatic reaction measurement for the sample in millivolts;
 $E_{cal1}$ = post-enzymatic reaction measurement for calibrator 1 in millivolts;
 Cal $1_{UN}$ = actual concentration of urea in calibrator 1 (known);
 Cal$_{1k}$ = actual concentration of potassium in calibrator 1 (known);
 k = potassium selectivity factor for the electrode;
 conc. K = concentration of potassium in the sample.

The selectivity factor k is determined experimentally for electrode 50 using calibrators having known concentrations of urea and potassium ions, and for this electrode is approximately 1/5, meaning that about five potassium ions in the sample are counted as one ammonium ion by the electrode.

The slope S is theoretically a constant equal to RT/ZF, where R is the universal gas constant, T is the temperature, Z is the ionic charge of the ion produced, and F is Faraday's constant. In practice, however, the value of S is determined from the calibration data according to the following equation:

$$S = WE_F / \log \frac{Cal\,1_{UN} + kCal\,1_k}{Cal\,2_{UN} + kCal\,2_k} \quad (2)$$

where k,
 Cal $1_{UN}$, and Cal $1_k$ are as defined in equation (1);
 Cal $2_{UN}$ = actual concentration of urea in calibrator 2 (known);
 Cal $2_k$ = actual concentration of potassium in calibrator 2 (known);
 W $E_F$ = difference in millivolts between the post-enzymatic reaction measurements for calibrators 1 and 2.

The concentration of potassium in the sample (conc. K) is determined from the pre-enzymatic reaction data obtained from the two calibrators and the sample using the Nicolsky equation. Because urea is not converted to ammonium ions during the pre-enzymatic reaction cycle, the Nicolsky equation reduces to the following form:

$$\text{conc. } K = \text{antilog} \frac{WE_B}{S^1} * Cal\,1_k \quad (3)$$

where
 Cal $1_k$ is as defined in equation (1);
 $WE_B$ = difference in millivolts between the pre-enzymatic reaction measurements of the sample and calibrator 1; and
 $S^1$, like slope S, is theoretically a constant, but in practice is determined experimentally from the pre-enzymatic reaction calibration data according to the following equation:

$$S^1 = WE_B / \log \frac{Cal\,1_k}{Cal\,2_k} \quad (4)$$

where
 Cal $1_k$ and Cal $2_k$ are as defined in equation 2;
 $WE_B$ = difference in millivolts between the pre-enzymatic reaction measurements of calibrators 1 and 2.

Thus, by using equations 1-4, and obtaining pre-enzymatic reaction measurements for the two calibrators and sample, and post-enzymatic reaction measurements for the two calibrators and sample, the actual urea concentration in the sample is obtained.

In a specific example, 12 microliters of sample and 450 microliters of a buffered calibration solution (Tris-HCl buffer, pH 7.5) having a potassium ion concentration of 8 millimols per liter and a urea concentration of 50 milligrams per deciliter were placed in mixing station 12. After mixing, the diluted solution was then pulled from station 12 into reaction coil 92 and the analysis and reference regions of electrodes 44, 56 at a rate of about 190 microliters per second using positive displacement pump 64. Pump 64 then was operated to produce back and forth (oscillating) flow of the calibration solution for thirteen seconds after which a pre-enzymatic reaction measurement (ten data points taken at 100 millisecond intervals) was taken at electrodes 50, 56. After pre-enzymatic reaction data had been collected, the calibration solution was pulled from the reaction coil 92 and positioned in the analysis and reference regions of electrodes 50, 56 at a rate of about 190 microliters per second, and pump 64 was again operated to oscillate the calibration solution for about eight seconds. A second set of ten measurements, representing post-enzymatic reaction data, was then taken. After collection of this data, the first calibration solution was removed and the flow path washed for about nine seconds with Tris-HCl buffer solution to remove traces of the calibrator solution.

Following the buffer rinse, the procedure was repeated with a second buffered calibration solution having a potassium ion concentration of 2 millimols per liter and a urea concentration of 20 milligrams per deciliter to obtain pre-enzymatic reaction and post-enzymatic reaction data on the second calibration solution.

A twelve microliter volume of serum sample diluted with 450 microliters of Tris-HCl buffer (0.05 M, pH 7.5±0.01) was then placed in mixing station 12 and similarly flowed through the reaction chamber 92 and analysis and reference regions of electrodes 50, 56 and pre-enzymatic (background) and post-enzymatic reaction data similarly collected. At the end of the data collection, the data was analyzed to obtain the actual urea concentration of the serum sample in accordance with the above data analysis procedure.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. A system for analyzing a biological fluid for a constituent of interest comprising
    structure defining a sample inlet port,
    structure defining an analysis region, a measuring system connected in sensing relation to said analysis region,
    structure defining a reaction chamber, series flow path structure connecting said reaction chamber structure to said analysis region structure,
    an immobilized enzyme in said reaction chamber capable of modifying said constituent of interest,
    means connecting said sample inlet port structure to said reaction chamber,
    liquid flow means including a positive displacement pump that is connected to said series flow path structure and that has has a unidirectional sample flow mode and a bidirectional sample flow mode, and
    control means for sequentially operating said liquid flow means in said unidirectional sample flow mode to initially flow sample material to be analyzed from said sample inlet port to said reaction chamber and said analysis region,
    operating said liquid flow means in said bidirectional sample flow mode to oscillate the sample material through said reaction chamber and facilitate modification by said immobilized enzyme of said constituent of interest in said sample material without introducing modified sample material into said analysis region,
    operating said measuring system to obtain a first measurement of unmodified sample material in said analysis region,
    operating said liquid flow means in a unidirectional sample flow mode to flow modified sample material from said reaction chamber to said analysis region,
    operating said measuring system to obtain a measurement of modified sample material in said analysis chamber, and
    operating said measuring system to provide an indication of the amount of said constituent of interest in said sample material as a function of said measurements of said unmodified and modified sample material.

2. The system of claim 1 wherein said analysis region and said reaction chamber each have an inlet and an outlet, the outlet of said reaction chamber is connected to the inlet of said analysis region, and
    said control means operates said pump in said unidirectional sample flow mode to initially flow sample material to be analyzed from said sample inlet port through said reaction chamber to said analysis region at a flow rate of at least about one hundred microliters per second.

3. The system of claim 1 wherein said measuring system includes two electrodes for measuring different constituents of interest in said sample, at least one of said electrodes being an ion selective electrode.

4. The system of claim 1 wherein said measuring system includes a measuring electrode and said analysis region also has a reference electrode connected thereto, and said measuring and reference electrodes are spaced from one another by a flow path portion located so that said reference electrode is downstream of and spaced from said measuring electrode.

5. The system of claim 1 wherein said constituent of interest is urea, and said measuring system includes an ammonium ion selective electrode.

6. The system of claim 5 wherein the enzyme immobilized in said reaction chamber is urease enzyme, and said ammonium ion selective electrode includes nonactin.

7. The system of claim 1 wherein said constituent of interest is glucose, and said measuring system includes an oxygen sensing electrode.

8. The system of claim 7 wherein the enzyme immobilized in said reaction chamber is glucose oxidase enzyme, and said oxygen sensing electrode is of the polarographic electrode.

9. The system of claim 1 wherein said reaction chamber is in the form of an elongated tube.

10. The system of claim 9 wherein said reaction chamber tube is disposed in serpentine form on a temperature stabilizing member.

11. The system of claim 1 wherein said analysis region is in a flow-through cell, said cell includes structure defining an inlet port, an outlet port, and at least two sensor accepting ports, means defining a sample flow path through said flow-through cell and serially connecting said inlet port, said sensor accepting ports and said outlet port, and including a first serpentine flow path portion between said inlet port and a first sensor accepting port and a second serpentine portion between a second sensor accepting port and said outlet port, said sample flow path being disposed in a generally vertical plane.

12. The system of claim 11 wherein each said serpentine flow path portion includes a downwardly curved portion and an upwardly curved portion.

13. The system of claim 12 wherein said sample flow path includes a first section that extends generally upwardly from said first serpentine flow path portion to a first sensor accepting port, a second section that extends generally downwardly from a second sensor accepting port to said second serpentine flow path portion, and an isolation portion that extends from said first section to said second section and is inclined generally downwardly to provide an isolation section between said first and second portions.

14. The system of claim 1 and further including housing structure in which said analysis region and said reaction chamber are housed, and means to control the temperature of said housing structure so that said analysis region and said reaction chamber are in a temperature controlled environment.

15. The system of claim 14 wherein said reaction chamber is in the form of an elongated tube.

16. The system of claim 15 wherein said reaction chamber tube is disposed in coil form on a cylindrical temperature stabilizing member.

17. The system of claim 15 wherein said analysis region also has a reference electrode connected thereto, and said measuring and reference electrodes are spaced from one another by a flow path portion located so that said reference electrode is downstream of and spaced from said measuring electrode.

18. The system of claim 17 wherein said analysis region is in a flow-through cell, said cell includes structure defining an inlet port, an outlet port, and at least two sensor accepting ports, means defining a sample flow path through said flow-through cell and serially connecting said inlet port, said sensor accepting ports and said outlet port, and including a first serpentine flow path portion between said inlet port and a first sensor accepting port and a second serpentine portion between a second sensor accepting port and said outlet port, said sample flow path being disposed in a generally vertical plane.

19. The system of claim 18 wherein each said serpentine flow path portion includes a downwardly curved portion and an upwardly curved portion.

20. The system of claim 19 wherein said sample flow path includes a first section that extends generally upwardly from said first serpentine flow path portion to a first sensor accepting port, a second section that extends generally downwardly from a second sensor accepting port to said second serpentine flow path portion, and an isolation portion that extends from said first section to said second section and is inclined generally downwardly to provide an isolation section between said first and second portions.

21. The system of claim 20 wherein said measuring system includes two electrodes for measuring different constituents of interest in said sample, at least one of said electrodes being an ion selective electrode.

22. The system of claim 21 wherein said constituents of interest are urea and glucose, and said electrodes include an ammonium ion selective electrode and an oxygen sensing electrode.

23. The system of claim 22 wherein glucose oxidase and urease enzymes are coimmobilized in said elongated tube.

* * * * *